United States Patent [19]
Herbst et al.

[11] Patent Number: 5,816,806
[45] Date of Patent: Oct. 6, 1998

[54] DENTAL INSTRUMENTS WITH LARGE MOLDED HANDLES

[75] Inventors: Walter B. Herbst, Lake Forest; David A. Demar, Aurora; William E. Hess, Chicago, all of Ill.

[73] Assignee: Hu-Friedy Mfg. Co., Inc., Chicago, Ill.

[21] Appl. No.: 688,865

[22] Filed: Jul. 31, 1996

[51] Int. Cl.$^6$ .................................................. A61C 17/00
[52] U.S. Cl. ............................................................ 433/141
[58] Field of Search .................................... 433/141, 142, 433/143, 144, 145, 146, 147

[56] References Cited

U.S. PATENT DOCUMENTS

| | | | |
|---|---|---|---|
| D. 249,062 | 8/1978 | Grafoord et al. | 433/141 X |
| 2,818,647 | 1/1958 | Berliner | 433/143 |
| 4,060,897 | 12/1977 | Greenstein | 433/141 X |
| 4,759,713 | 7/1988 | Heiss et al. | 433/141 |
| 4,795,344 | 1/1989 | Brewer, Jr. | 433/141 X |

OTHER PUBLICATIONS

Hu–Friedy Colours Dental Instrument Catalog in Dutch, published before filing date of patent application (Jul. 31, 1996).

American Eagle Dental Instrument Catalog, published before filing date of patent application (Jul. 31, 1996).

Primary Examiner—Nicholas D. Lucchesi
Attorney, Agent, or Firm—Rockey, Milnamow & Katz, Ltd.

[57] ABSTRACT

A dental instrument with a large injection molded plastic handle has an elongated generally cylindrical symmetrical shape with first and second spaced apart ends. Anti-slip peripheral groves or slots are molded into the handle adjacent the first and second ends. Subsequent to the molding process, knurls are applied adjacent the first and second ends to improve the anti-slip characteristics of the handle. At least some of the knurling is positioned between the peripherally located grooves or slots. Stainless steel cones are affixed to the respective ends of the handle, either by ultrasonic welding or by positioning the cones in the molds, as inserts, and directly molding the plastic around retaining ends of the cones. Tips or points are press-fit and/or adhesively bonded into channels in the cones of the instrument. A single ended instrument carries a smooth, closed, cap at one of the ends.

51 Claims, 4 Drawing Sheets

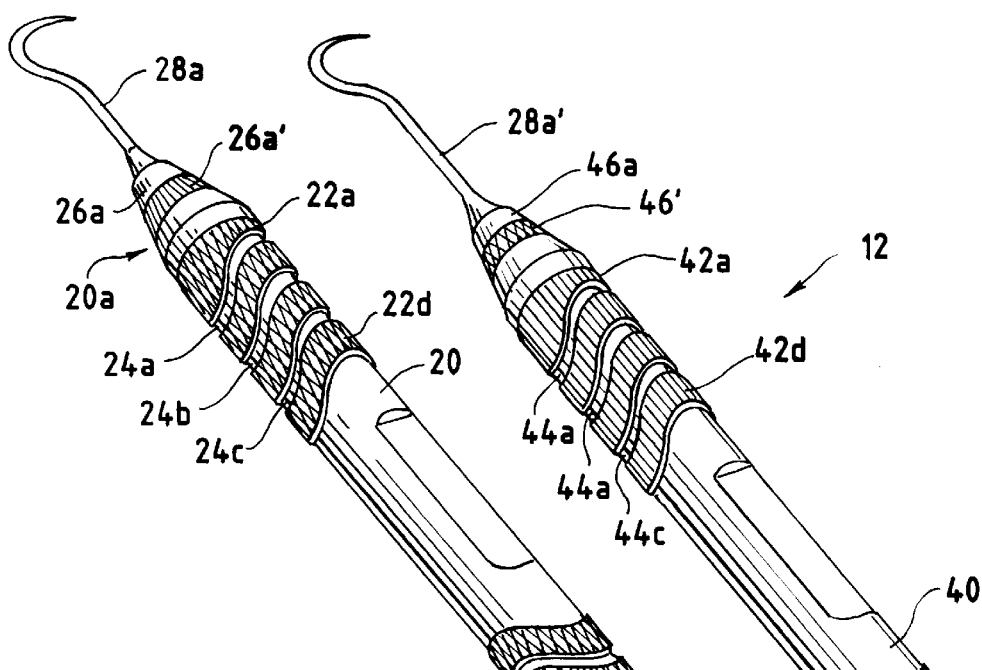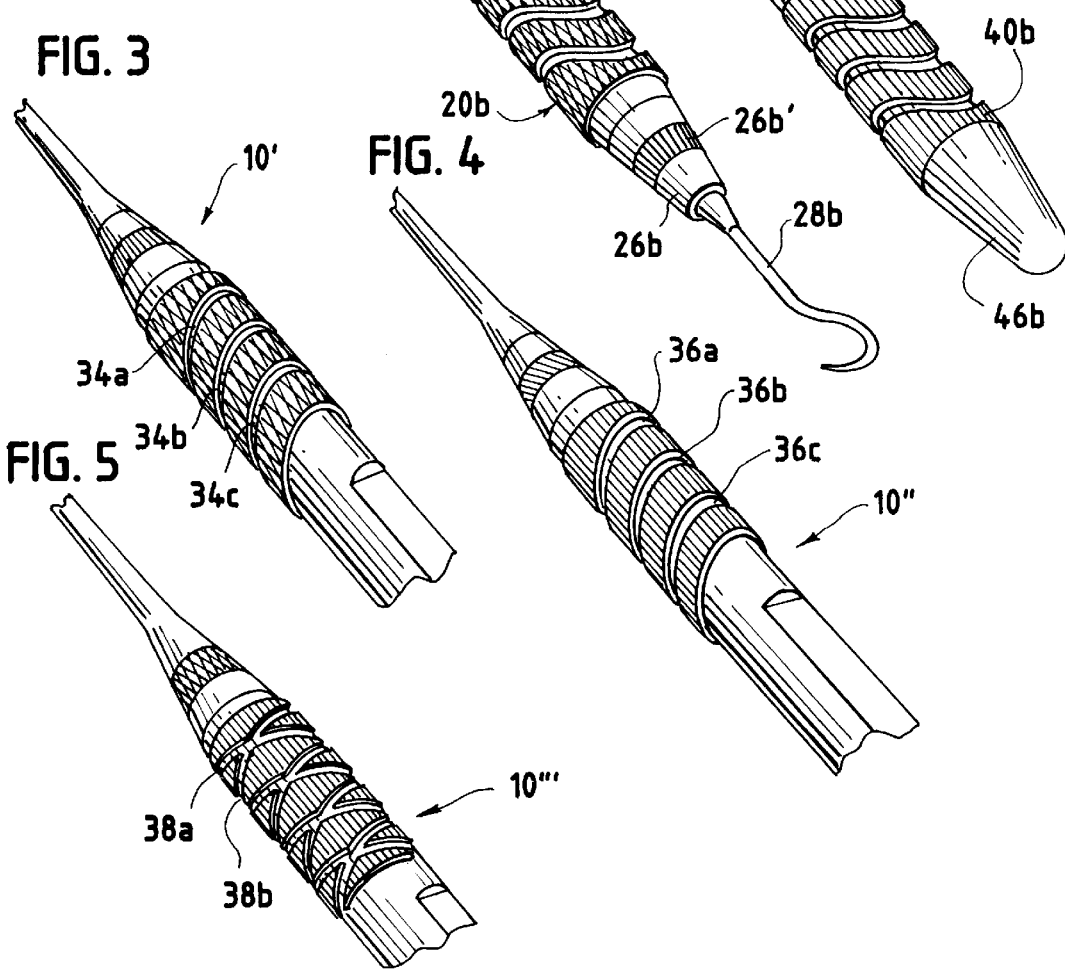

DENTAL INSTRUMENTS WITH LARGE MOLDED HANDLES

FIELD OF THE INVENTION

The invention pertains to dental instruments. More particularly, the invention pertains to hand-held dental instruments which have integrally molded handles.

BACKGROUND OF THE INVENTION

Hand-held dental instruments such as scalers, mirrors, probes and the like have long been known and are useful in connection with dental hygiene as well as diagnostic and restorative treatments. Many known instruments include elongated metal handles with the tips, or probes carried at the ends thereof. Additionally, single ended instruments, such as mirrors, have elongated metal handles with a mirror carried at an end thereof.

It has also been known to create dental instruments with non-metallic handles. These have been formed by machining preformed plastic stock to create a generally elongated, cylindrical, plastic handle. Points or mirrors have been affixed to the ends thereof.

Alternately, plastic handles have been formed by injection molding. It is also known to affix points or probes to the ends of injection molded handles.

Notwithstanding known instruments, there continues to be a need for instruments having molded handles which possess desirable ergonomic parameters. Preferably, such instruments will be easy to pick up and use, and will include features to minimize both axial and rotary slippage of the instrument in the gloved fingers of a practitioner when the instrument is in use. Also, it would be preferable if such instruments would have extensive useable lives, permitting numerous sterilization cycles without breaking down or exhibiting discoloration.

SUMMARY OF THE INVENTION

Dental instruments in accordance with the present invention include large, generally cylindrical, elongated injection molded handles in single ended or double ended varieties. Preferably, handle diameter will equal or exceed ⅜ of an inch. Such instruments include non-molded knurling which can be applied to an injection molded handle in a subsequent operation.

An asymmetrically located gate can be provided for injecting the plastic into the mold for a handle. The subsequent knurling operation, in addition to providing non-slip surfaces for the handle, also eliminates visual evidence of the molding gate.

In one aspect, stainless steel cones can be carried on first and second spaced apart ends of the handle. The cones can be inserted into a pre-molded handle and attached thereto by ultrasonic welding and/or adhesive. Alternately, the cones can be positioned as inserts in the mold and the handle directly molded thereto during the manufacturing process.

If desired, a single insert can be provided which includes first and second spaced apart stainless steel cones joined by a stainless steel center member, such as a rod. This element can inserted into the mold and the handle molded around same.

Selected points or tips can be press-fit into the stainless steel cones. Knurling can also be applied to the cones prior to either attaching the cones to a previously molded handle or using the cones as an insert in the mold.

In yet another aspect, the plastic can be color coded prior to the molding step. This results in a plurality of coded, visually discernable handles which can be associated with different types of points or tips for the convenience of practitioners.

A single ended instrument, such as a mirror, can be formed with a molded handle. The other end of the handle carries a plastic cap. The cap can be integrally molded or can be separately molded and attached to the handle.

In yet another aspect, gripping groves or slots can be molded in the plastic to enhance gripability and to provide additional resistance to slippage when the practitioner is using the instrument. The groves can be of various shapes. They extend circumferentially about the periphery of at least one of the ends of the handle. The knurling can be applied to spaces between the groves. Since the knurling is applied after the molding step, the same mold can be used for very different handles.

Numerous other advantages and features of the present invention will become readily apparent from the following detailed description of the invention and the embodiments thereof, from the claims and from the accompanying drawings.

BRIEF DESCRIPTION OF THE DRAWING

FIG. 1 is a perspective view of a dental instrument with a molded handle in accordance with the present invention;

FIG. 2 is a perspective view of a single and a dental instrument with an enlarged, molded, handle illustrating a different style of knurling;

FIG. 3 is a fragmentary perspective view, enlarged, of a portion of an end of a dental instrument illustrating a different form of groves;

FIG. 4 is a fragmentary, enlarged, perspective view of a portion of an end of a dental instrument illustrating a different combination of groves and knurlings;

FIG. 5 is a fragmentary, enlarged, perspective view of a portion of an end of a dental instrument illustrating and yet a different combination of groves and knurlings;

DETAILED DESCRIPTION OF THE PREFERRED EMBODIMENTS

Figure 6:
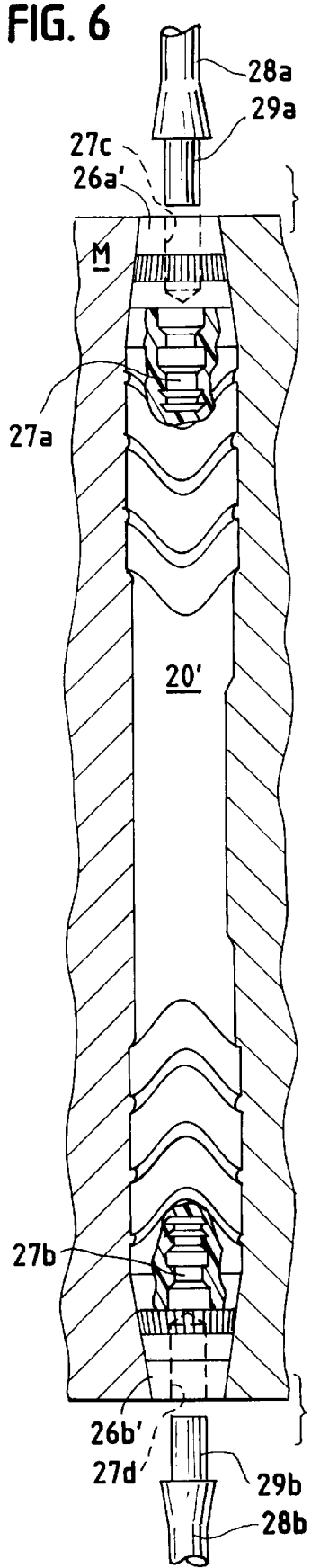
FIG. 6 illustrates a method of manufacturing a dental instrument, such as a dental instrument of FIG. 1.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

With respect to FIGS. 1 and 2, dental instruments 10 and 12 respectively are illustrated therein. The dental instrument 10 is a double ended instrument. The instrument 12 is a single ended instrument. It will be understood that the particular tip that is used is not a limitation of the present invention.

The instrument 10 includes a large, elongated, generally cylindrical injection molded handle 20. The handle 20 has first and second ends 20a, 20b. Each of the ends 20a, 20b exhibits a plurality of ridges, such as the ridges 22a through 22d which are carried on the end of 20a. The ridges 22a. . . 22d are separated from one another by serpentine peripheral groves or depressions 24a, 24b and 24c. The ridges 22a–22d are molded along with the handle 20 as are the groves or depressions 22a, 24c.

Each of the ridges 22a. . . 22d extends circumferentially about the handle 20. Each of the ridges 22a. . . 22d is processed after the handle 20 is extracted from the mold in a knurling operation. As a result of this operation, each of the ridges 22a. . . 22d carries a plurality of knurls which in the case of the dental instrument 10 are generally diamond shaped. As discussed subsequently and as will be understood by those of skill in the art, different styles of knurling can be used without departing from the spirit and scope of the present invention.

The handle 20 can be molded for example, of a polyetherimide (available under the ULTEM brand name). Alternately, a polyethersulphone can be used. Other medical grade plastics can be used provided they exhibit similar properties such as heat and stain resistance.

In a preferred embodiment, the handle 20 has a diameter on the order of ⅜ of an inch or larger. The diamond shaped knurls of FIGS. 1 can be applied in various sizes.

Carried adjacent to each of the ends, 20a, 20b is a tip or probe receiving cone, 26a, 26b. The cones 26a, 26b can be formed, for example of stainless steel.

Each of the cones carries a preformed channel (illustrated in phantom in FIG. 6) into which a respective tip or probe 28a, 28b can be inserted with a press-fit. In addition, if desired, adhesives could also be used. Alternately, the tips 28a, 28b and respective channels can be threaded for rotatable engagement.

The cones 26a, 26b can be inserted into the ends 20a, 20b of the handle 20, subsequent to extracting the handle 20 from the mold, and ultrasonically welded thereto. Alternately, the cones 26a, 26b can be located in the mold, as inserts prior to the injection step. When plastic is injected into the mold, that plastic fills in the voids and recesses at the base of the cones 26a, 26b and thereby locks the cones to the respective ends of the handle 20a, 20b.

Each of the cones 26a, 26b carries a knurled region 26a', 26b'. The added knurling in the cones 26a, 26b enhances non-slip gripping of the instrument 10 by a dental practitioner.

It will be understood by those of skill in the art that a variety of tips or probes, corresponding to the tips 28a, 28b could be used with the instrument 10 without departing from the spirit and scope of the present invention.

The handle 20 in addition to providing enhanced gripability and enhanced resistance to slippage also reduces practitioner fatigue due to the diameter. In addition, the size and texture of the handle 20 permits a practitioner to hold and control the instrument with less force than might otherwise be required.

The single ended instrument 12 of FIG. 2 includes a large, elongated, generally cylindrical injection molded handle 40. The handle 40 has first and second ends 40a, 40b. The ends 40a, 40b each carry a plurality of circumferential, spaced apart ridges 42a. . . 42d.

The ridges 42a. . . 42d are spaced apart by molded groves or slots 44a, 44b and 44c. As was the case with the groves or slots 24a. . . 24c, the groves 44a. . . 44c extend circumferentially around the handle 40.

Knurls are formed on the ridges 42a. . . 42d subsequent to the molding step as discussed above with respect to the instrument 10. As is illustrated in FIG. 2, the instrument 12 may carry a plurality of straight line knurls unlike the diamond shaped knurls of the instrument 10 of FIG. 1. As will be understood by those of skill in the art, the knurls could be formed in only one end of a single ended instrument.

The instrument 12 carries a stainless steel cone 46a adjacent to the end 40a. It carries a molded end cap 46b adjacent the end 40b. The stainless steel cone, as described above with respect to the cone 26a, can be ultrasonically welded or integrally molded to the handle 40. A tip or mirror 28a', can be press-fit or threaded into a corresponding channel in the stainless steel cone 46a. The stainless steel cone 46a also carries knurling 46' to improve its non-slip characteristics.

FIGS. 3 through 5 illustrate alternate embodiments of the instruments 10, 12. The instruments 10' and 10" of FIGS. 3, 4, carry molded groves 34a–34c and 36a–36c in the form of a helix. The instrument 10 '" of FIG. 5 carries a double helix 38a, 38b. As is illustrated by FIGS. 3–5, various kinds of knurling can be used since the knurls are the result of a post-molding operation.

FIG. 6 illustrates various aspects of the process of making an instrument, such as the instrument 10. FIG. 6 illustrates a mold M wherein the cones, such as the cones 26a', 26b' are positioned in the mold as inserts, prior to injecting plastic therein.

As illustrated in FIG. 6, the cones each carry locking stems, such as the stems 27a and 27b. These stems extend toward one another when the cones 26a' and 27b' are inserted into the mold M. When the plastic for the handle 20' is injected into the mold M the fluid handle material fills in the regions around the stems 27a and 27b and solidifies. This permanently attaches the cones 26a' and 26b' to the handle 20'.

The tips, such as tips 28a', 28b ' can be inserted into the cones 26a, 26b, either before or after the molding step without departing from the spirit and scope of the present invention. Each of the tips or probes carries a cylindrical stud, such as studs 29a, 29b which are inserted with a press-fit into respective channels 27c and 27d (illustrated in phantom in FIG. 6). Alternately, the studs 29a, 29b can be threaded and the channels 27c, 27d can carry mating threads to rotatably couple the tips or points to the handle 20'.

Figure 7:
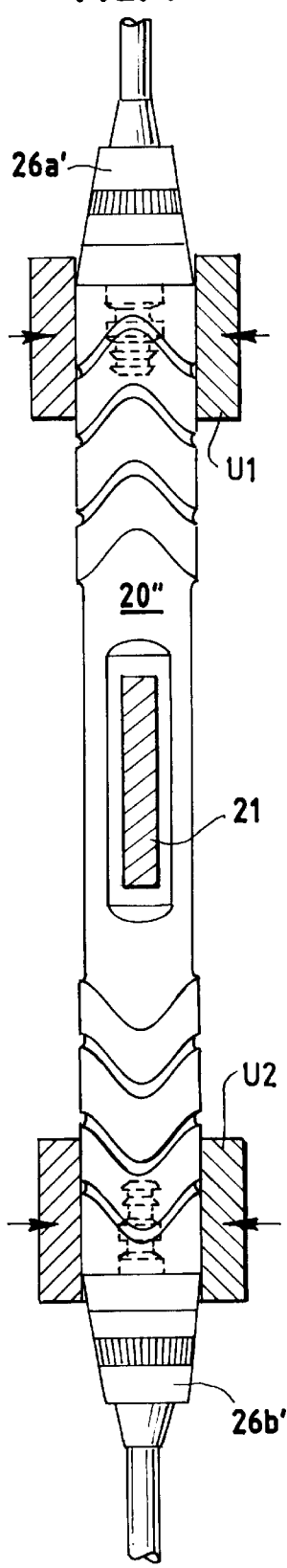
FIG. 7 illustrates, schematically, an alternate method of manufacturing a dental instrument.

FIG. 7 illustrates an alternate method of making an instrument, such as the instrument 10. In the method illustrated in FIG. 7, a previously molded handle 20" receives cones 26a' and 26b'. The stems, such as stems 27a and 27b are press-fit into channels molded into the ends of the handle 20".

In an ultrasonic welding step, ultrasonic energy is applied to the handle 20" (illustrated schematically by fixtures U1 and U2). The applied ultrasonic energy heats, softens and permits the plastic in the handle 20", which is subject to the applied ultrasonic energy, to flow around and enclose the stems 27a, 27b thereby permanently attaching the cones 26a' and 26b' thereto.

Because the handle 20" is injection molded, a representation of corporate name, logo or other symbols 21 can be molded in at the same time that the handle is molded. This eliminates a secondary step.

Figure 8:
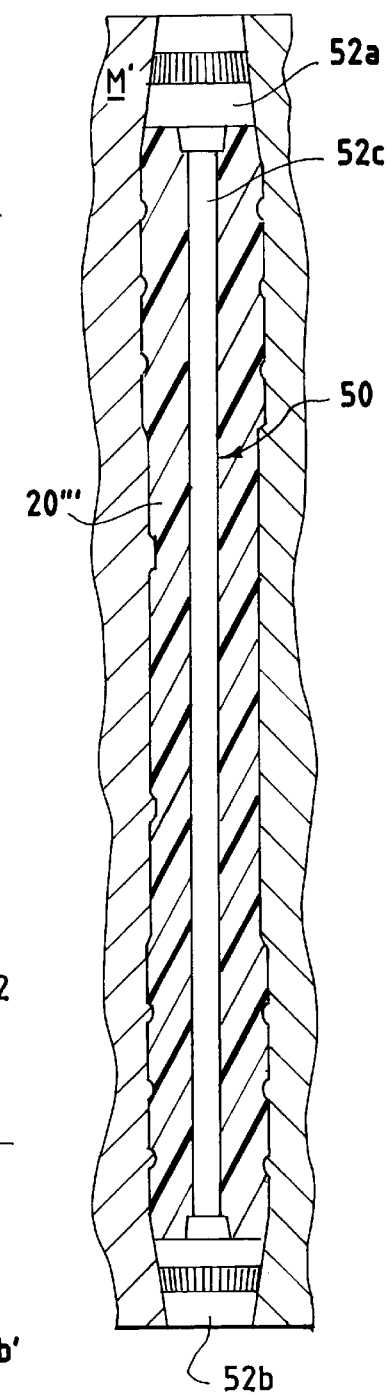
FIG. 8 illustrates yet another method of manufacturing a dental instrument.

FIG. 8 illustrates yet another method of making an instrument, such as the instrument 10. In the method of FIG. 8, an elongated insert 50 is positioned in a mold M'. The insert 50 includes first and second spaced apart conical end members 52a, 52b. The conical end members 52a, 52b are joined by a rigid rod or stem 52c.

When the material is injected into the mold M', thereby forming handle 20''', the insert stem 52c is surrounded by and embedded in the plastic material. That material also fills any voids or spaces at the bases of the cones 52a, 52b thereby forming the molded handle 20'''. The handle 20''' has integrally attached tip or probe mounting cones 52a, 52b.

The inserted rod method of molding, FIG. 8, reduces the amount of plastic that is required. It also has the potential to increase the flexural strength of the handle.

As will be understood by those of skill in the art, these inserts as illustrated in FIGS. 6 and 8 can be expected to reduce both time and cost in manufacturing. It will be understood that other manufacturing steps could be incorporated into the process of manufacturing instruments, such as the instruments 10, 12 without departing from the spirit and scope of the present invention.

Figure 9:
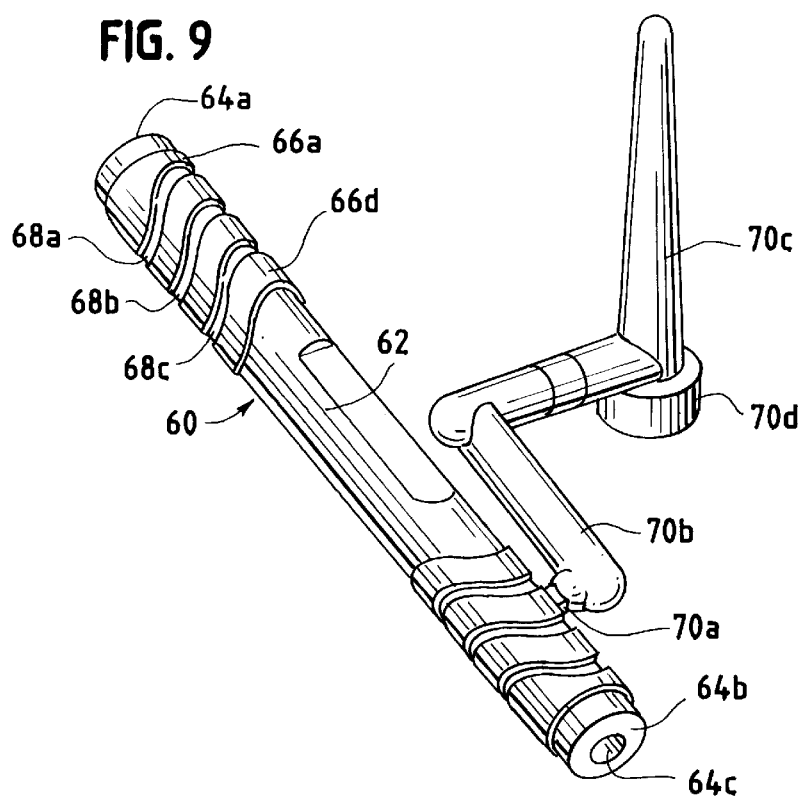
FIG. 9 is a perspective view of a molded handle subsequent to being removed from a mold.
Figure 10:
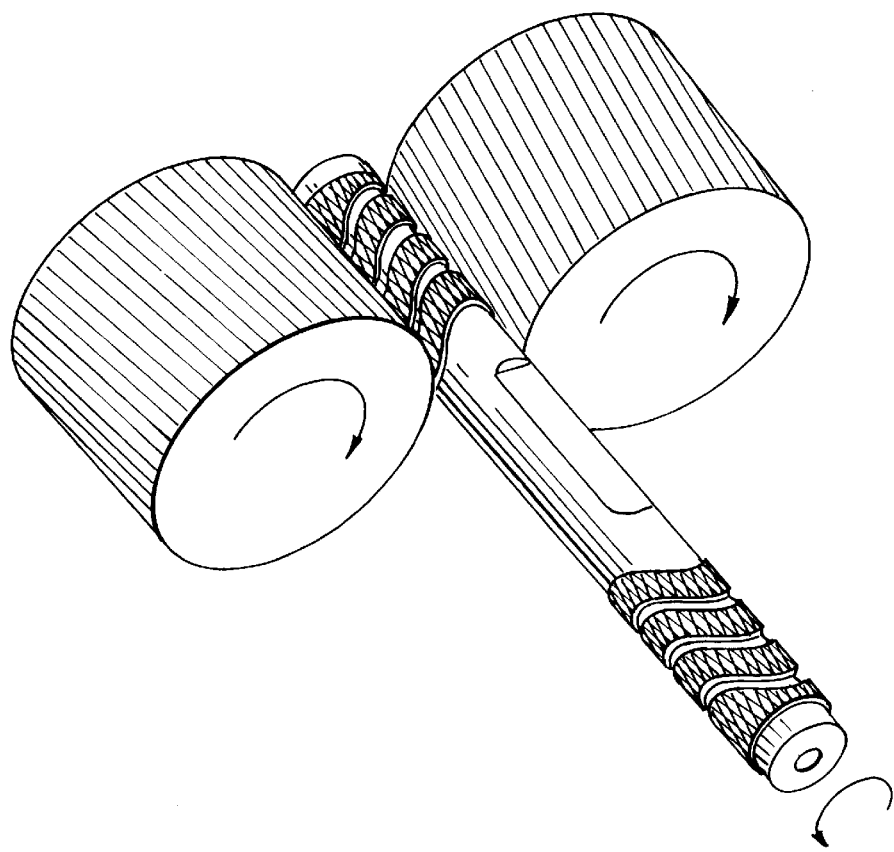
FIG. 10A is a perspective schematic view of knurling being applied to the molded handle of FIG. 9.
FIG. 10B is a view of another method of applying knurling to the molded handle of FIG. 9.
Figure 11:
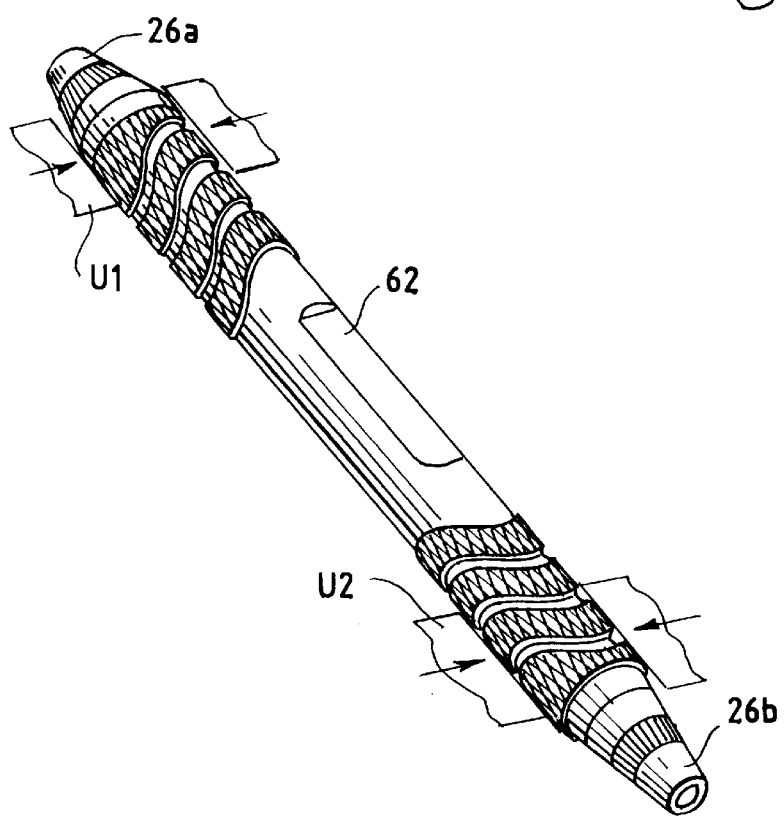
FIG. 11 is a perspective view of the handle of FIG. 10 with cones being affixed thereto.

FIGS. 9 through 11 illustrate other aspects of manufacturing instruments, such as the instruments 10, 12. FIG. 9 illustrates a molded part 60, which after further processing forms a handle. The part 60, upon being ejected from the mold, such as the mold M, has an elongated cylindrical body portion 62 with first and second ends 64a, 64b.

An axially directed channel, such as the channel 64c, has been molded into each of the ends 64a, 64b. Further, each of the ends carries molded elevated regions, such as the regions 66a. . . 66d. The regions 66a. . . 66d are separated by molded groves 68a, 68b and 68c.

In accordance with the present invention, an asymmetrically located gate 70a provides an injection port through which the plastic material is injected into the voids of the mold M and to which the runner 70b is attached. As will be understood by those of skill in the art, attached to the runner 70b are a sprue 70c and a cold plug well 70d. The runner 70b and attached surplus plastic is removed from the body 62 subsequent to the part 60 being extracted from the mold M.

Figure 10A:
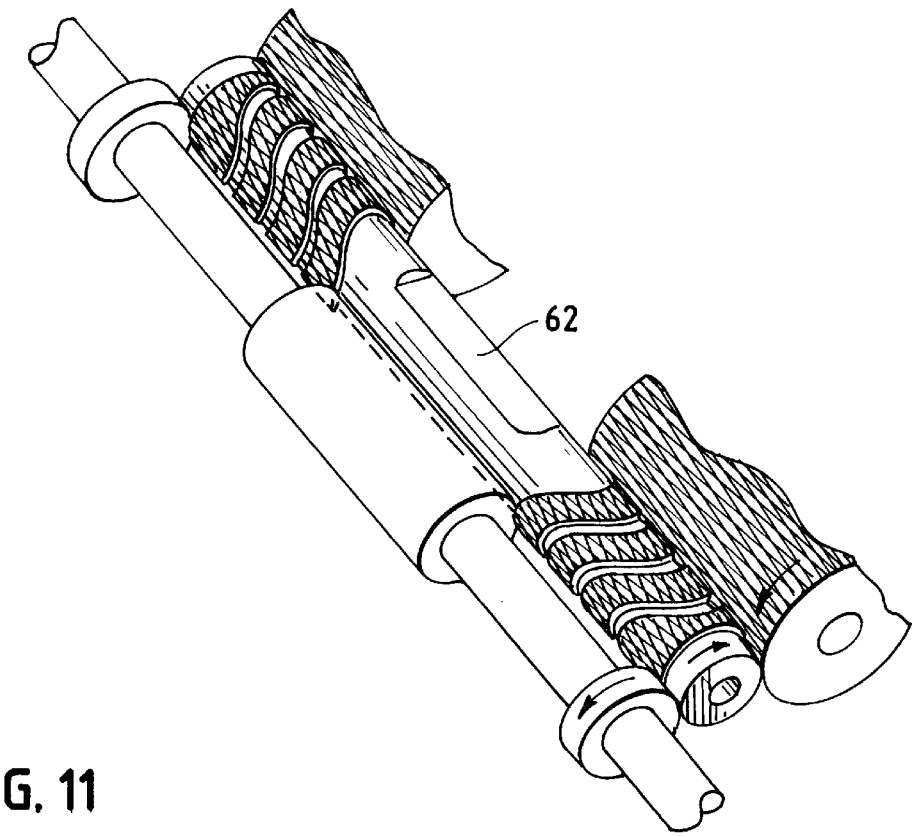

FIG. 10A illustrates, schematically, a process of knurling the body 62. Since the knurls are formed on the body 62 subsequent to the molding step, the same molded part can be customized for a variety of different practitioners simply by changing the fixtures used in the knurling step. FIG. 10B illustrates another process of knurling the body 62.

FIG. 11 illustrates a step of ultrasonic welding the stainless steel cones, such as the cones 26a and 26b to the molded part 62 to complete the manufacturing process. As illustrated in FIG. 11, the tips or points 28a, 28b can subsequently be installed in the cones 26a26b.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A dental instrument comprising:
   an elongated, injection molded plastic handle having a longitudinal axis with non-molded knurling formed at least on a selected region thereof said selected region defined by a band which wraps around said plastic handle and having length dimension at an oblique angle to said longitudinal axis; and
   a selected working element carried on the handle.

2. An instrument as in claim 1 wherein the working element includes a conical metal portion non-adhesively attached to an end of the handle.

3. A dental instrument as in claim 2 wherein the metal portion includes a cylindrical attachment stem which extends into a channel formed in the end of the handle and wherein the stem is locked to the handle by surrounding plastic.

4. The instrument of claim 1 which includes molded, spaced apart, gripping depressions with the non-molded knurling located therebetween.

5. An instrument as in claim 1 wherein the molded body, at least in part, has a diameter in excess of ⅜ of an inch.

6. An instrument as in claim 1 wherein the handle has first and second ends, a plurality of molded grooves adjacent to one of the ends and wherein the working element extends from the one end.

7. An instrument as in claim 6 which includes a molded plastic cap carried on the other of the ends.

8. An instrument as in claim 6 wherein the knurling is formed between spaced apart grooves.

9. An instrument as in claim 6 wherein the grooves circumferentially enclose the handle.

10. An instrument as in claim 6 wherein the handle includes an integrally formed color coded indicator.

11. A dental instrument as in claim 1 wherein the plastic is selected from a class which includes a polyethermide and a polyethersulphone.

12. A dental instrument comprising:
    an elongated, injection molded plastic handle having a longitudinal axis with non-molded knurling formed at least on a selected region thereof; and
    a selected working element carried on the handle, and wherein an injection port is located, during molding, on the selected region said selected region defined by a band which wraps around said plastic handle and having a length dimension at an oblique angle to said longitudinal axis whereupon, when forming the non-molded knurling visual indication of the port is removed.

13. A dental instrument comprising:
    an elongated, injection molded plastic handle with non-molded knurling formed at least on a selected region thereof; and
    a selected working element carried on the handle;
    wherein the working element includes a conical metal portion non-adhesively attached to an end of the handle; and
    wherein the conical metal portion includes a knurled region.

14. A dental instrument as in claim 13 wherein the non-molded knurling on the handle and the knurling on the conical metal portion have different patterns.

15. A dental instrument as in claim 1 wherein the non-molded knurling is formed on the handle, after the molding step, using a screw machine.

16. An instrument comprising:
    an elongated, cylindrical, injection molded handle with at least a ⅜ inch diameter wherein the handle includes a molded, elevated, circumferential region interrupted by a series of molded circumferential grooves and wherein an injection site is located on the elongated region;

a working member carried at the end and fixedly attached to the handle wherein the member carries a plurality of friction providing surface discontinuities.

17. An instrument as in claim 16 which includes a plurality of friction providing surface discontinuities formed on the elevated region subsequent to molding the handle thereby eliminating visual indications of the injection site.

18. An instrument as in claim 16 wherein the handle carries a molded cap at one end and a tip at the other end.

19. An instrument as in claim 18 wherein the cap is integrally molded with the handle.

20. A method of making a dental instrument comprising:

injection molding an elongated, plastic, symmetrical instrument handle with raised, circumferential end regions wherein the end regions are interrupted, in an axial direction, by molded grooves and wherein the plastic is injected at an asymmetrically located port;

forming discontinuities on at least one of the end regions subsequent to the molding step, to improve gripability and to reduce slippage; and attaching at least one working element to an end of the handle adjacent to one of the end regions.

21. A method as in claim 20 which includes:

removing optically visible indications of the port during the forming step.

22. A method as in claim 20 which includes, in the forming step, producing selected knurls on the end regions.

23. A method as in claim 20 which includes coupling a metal conical element to one end of the handle.

24. A method as in claim 23 wherein the conical element is inserted into a mold and wherein a portion of the handle is formed therearound.

25. A dental instrument comprising:

an elongated, injection molded plastic handle with non-molded knurling formed at least on a selected region thereof; and a selected working element carried on the handle and wherein a grip motif is also molded into the handle, said selected region defined by a band which wraps around said plastic handle and has a length dimension at an oblique angle to said longitudinal axis.

26. A dental tool comprising:

an elongated plastic handle having a longitudinal axis and having at least one groove arranged around an outside surface of said handle, said groove having a portion which is at a substantially oblique angle to the axis of said handle; and a selected working element carried on said handle.

27. A tool as in claim 26 having knurling formed on the outside surface of said handle, adjacent to said groove.

28. A tool as in claim 27 wherein said knurling is machined knurling.

29. A tool as in claim 26 wherein said groove is one of a plurality of grooves, each of which have a substantially wavy shape around the outside of said handle.

30. A tool as in claim 26 wherein said one groove is continuous and spirals a plurality of times around said axis.

31. A tool as in claim 26 wherein said one groove is one of a plurality of grooves each of which is substantially arranged at an oblique angle to said axis.

32. A tool as in claim 31 wherein members of said plurality of grooves are spaced apart and have a parallel orientation.

33. A tool as in claim 31 wherein said plurality of grooves includes at least two grooves which intersect.

34. A tool as in claim 33 wherein said two grooves comprise a double helix configuration.

35. A tool as in claim 26 wherein said one groove has a substantially wavy shape around the outside of said handle.

36. A tool as in claim 35 wherein said one groove bounds in part non-molded knurling.

37. A tool as in claim 26 wherein at least one groove defines at least one annular region around the outside of said handle, said at least one annular region having a knurled surface, said at least one region has a non-uniform length in a direction parallel to the longitudinal axis.

38. A tool as in claim 26 wherein said selected working element is carried on a first end of said handle, and further comprising a second working element carried on a second, opposite end of said handle.

39. A tool as in claim 26 wherein said selected working element is carried on a first end of said handle, and an opposite, second end of said handle does not carry a working element.

40. A tool as in claim 26 wherein said handle is adapted to be gripped and manually driven to operate said working element.

41. A tool as in claim 26 wherein the working element extends from an end of the handle and is centrally located relative thereto with the at least one groove defining an axially oriented, variable length gripping region which carries a pattern therein.

42. A tool as in claim 41 wherein the pattern is not molded in the region.

43. A dental tool comprising:

an elongated plastic handle having a longitudinal axis;

a selected working element carried on said handle including a conical metal portion attached to an end of said handle, and an attached stem, wherein said conical metal portion is connected to an end of said attachment stem, wherein said attachment stem extends into a channel formed in the end of said handle and wherein said stem is locked to said handle by surrounding plastic.

44. A tool as in claim 43 wherein said conical metal portion includes a first knurled region.

45. A tool as in claim 44 wherein said handle includes at least one groove around an outside of said handle, and a second knurled region adjacent said conical metal portion, said second knurled region subdivided along said axis by said at least one groove.

46. A tool as in claim 44 wherein said first knurled region comprises axially oriented, straight knurls.

47. A tool as in claim 43 wherein said handle has at least a ⅜ inch diameter.

48. A tool as in claim 43 wherein said plastic is sterilizible, medical grade plastic.

49. A tool as in claim 43 wherein said plastic includes a pigment for color coding said tool.

50. A tool as in claim 43 wherein the handle includes at least one variable length region with knurling formed thereon.

51. A tool as in claim 43 further comprising a second working element carried on said handle including a second conical metal portion attached to an opposite end of said handle to said end, wherein said second conical, metal portion is connected to an opposite end of said attachment stem to said end of said attachment stem, said attachment stem being an elongated member.

* * * * *